(12) United States Patent  
Baumann

(10) Patent No.: US 12,140,747 B2  
(45) Date of Patent: Nov. 12, 2024

(54) LENS SYSTEM FOR A VIDEO ENDOSCOPE, ENDOSCOPE OBJECTIVE, VIDEO ENDOSCOPE, AND ASSEMBLY METHOD

(71) Applicant: KARL STORZ SE & Co KG, Tuttlingen (DE)

(72) Inventor: Harald Baumann, Tuttlingen (DE)

(73) Assignee: KARL STORZ SE & Co KG, Tuttlingen (DE)

( * ) Notice: Subject to any disclaimer, the term of this patent is extended or adjusted under 35 U.S.C. 154(b) by 226 days.

(21) Appl. No.: 17/104,312

(22) Filed: Nov. 25, 2020

(65) Prior Publication Data

US 2021/0157120 A1    May 27, 2021

(30) Foreign Application Priority Data

Nov. 26, 2019    (DE) .......................... 102019008226.5

(51) Int. Cl.
   *G02B 13/18*       (2006.01)
   *A61B 1/00*        (2006.01)
   (Continued)

(52) U.S. Cl.
   CPC ........ *G02B 23/243* (2013.01); *A61B 1/00197* (2013.01); *A61B 1/05* (2013.01);
   (Continued)

(58) Field of Classification Search
   CPC .... G02B 23/243; G02B 9/12; G02B 13/0035; G02B 13/18; G02B 23/2484; G02B 23/2407; A61B 1/00197; A61B 1/05
   See application file for complete search history.

(56) References Cited

U.S. PATENT DOCUMENTS 5,119,238 A      6/1992   Igarashi
5,175,650 A *   12/1992   Takayama ............ G02B 23/243
                                                                                 359/716

(Continued)

FOREIGN PATENT DOCUMENTS

DE        102005015145 A1    10/2006
EP          0587177 A1 *    9/1993

(Continued)

OTHER PUBLICATIONS

P.R. Yoder, Jr., Synopsis of Paper "Lens MountingTechniques," 1983, pp. 1-4 [online], [retrieved Nov. 8, 2022], retrieved from the Internet <URL: https://wp.optics.arizona.edu/optomech/wp-content/uploads/sites/53/2016/10/Synopsis-of-Paper-Michihisa-Onishi.pdf>. (Year: 1983).*

(Continued)

*Primary Examiner* — Cara E Rakowski
*Assistant Examiner* — Wesley Scott Ashton
(74) *Attorney, Agent, or Firm* — David N. Villalpando; Jacqueline Cohen

(57) ABSTRACT

A lens system (1) for a video endoscope comprises, in order from an object side, a cover glass (20), a first lens (40), a second lens (60) and one or more further lenses, wherein all lenses are single lenses. An aperture stop (21) is arranged at the object side of the first or the second lens (40, 60), all lenses on an image side of the aperture stop (21) are aspherical, all lenses are made of glass or of a crystalline material, and at least one lens has a refractive index n approximately equal to or exceeding 1.66. The invention also relates to an endoscope objective, to a video endoscope, and to a method for assembling an endoscope objective.

16 Claims, 3 Drawing Sheets

(51) Int. Cl.
  *A61B 1/05*    (2006.01)
  *G02B 9/12*    (2006.01)
  *G02B 13/00*   (2006.01)
  *G02B 23/24*   (2006.01)

(52) U.S. Cl.
  CPC ............ *G02B 9/12* (2013.01); *G02B 13/0035* (2013.01); *G02B 13/18* (2013.01); *G02B 23/2484* (2013.01)

(56) References Cited

U.S. PATENT DOCUMENTS

| | | |
|---|---|---|
| 5,305,147 A | 4/1994 | Hasegawa et al. |
| 5,436,767 A | 7/1995 | Suzuki et al. |
| 5,828,498 A | 10/1998 | Sekiya et al. |
| 5,892,630 A * | 4/1999 | Broome ............ G02B 23/2423 359/834 |
| 6,142,930 A * | 11/2000 | Ito ..................... A61B 1/00096 600/110 |
| 7,129,474 B2 * | 10/2006 | Kobayashi ............ G02B 7/025 250/234 |
| 7,477,461 B2 * | 1/2009 | Bareau ............... G02B 13/0035 359/716 |
| 8,368,786 B2 * | 2/2013 | Fukuta ................. H04N 23/54 348/294 |
| 8,936,371 B2 * | 1/2015 | Maruyama ........ H01L 27/14627 359/601 |
| 9,257,470 B2 | 2/2016 | Ueno et al. |
| 9,372,336 B2 * | 6/2016 | Murata ................ G02B 23/243 |
| 2004/0160682 A1 * | 8/2004 | Miyano .................... G02B 9/12 359/784 |
| 2004/0196575 A1 * | 10/2004 | Nozawa ................... G02B 9/12 359/791 |
| 2004/0223068 A1 * | 11/2004 | Kamo ................. H04N 5/22521 348/E5.025 |
| 2005/0225872 A1 * | 10/2005 | Uzawa ..................... G02B 9/12 359/661 |
| 2008/0075442 A1 * | 3/2008 | Yamashita ............. H04N 23/57 396/25 |
| 2008/0174886 A1 * | 7/2008 | Sato ........................ G02B 13/18 359/754 |
| 2008/0225410 A1 * | 9/2008 | Ning ...................... G02B 7/022 359/830 |
| 2008/0225419 A1 * | 9/2008 | Kim .................... G02B 26/0825 359/847 |
| 2008/0266680 A1 * | 10/2008 | Chiang ................. G02B 7/021 359/819 |
| 2009/0034098 A1 * | 2/2009 | Aoi ....................... G02B 13/006 359/716 |
| 2009/0161234 A1 | 6/2009 | Sasamoto |
| 2010/0060996 A1 * | 3/2010 | Ozaki .................... G02B 13/18 359/773 |
| 2010/0245653 A1 * | 9/2010 | Bodor .................. G02B 23/243 348/335 |
| 2011/0043932 A1 * | 2/2011 | Nomura ................. G02B 7/026 359/819 |
| 2011/0286112 A1 * | 11/2011 | Orihara .............. G02B 13/0035 359/716 |
| 2012/0007972 A1 | 1/2012 | Uzawa |
| 2012/0016199 A1 | 1/2012 | Baba et al. |
| 2013/0271641 A1 * | 10/2013 | Calvet .................... G02B 7/028 348/340 |
| 2014/0104691 A1 * | 4/2014 | Chang .................... G02B 7/021 359/611 |
| 2014/0104707 A1 | 4/2014 | Nakamura et al. |
| 2015/0077622 A1 | 3/2015 | Jeno et al. |
| 2016/0161699 A1 * | 6/2016 | Kim ....................... G02B 7/022 359/784 |
| 2016/0235282 A1 | 8/2016 | Nakamura |
| 2018/0011280 A1 * | 1/2018 | Sung ..................... G02B 7/021 |
| 2018/0246295 A1 | 8/2018 | Kubota et al. |
| 2018/0307010 A1 | 10/2018 | Amani et al. |
| 2018/0359396 A1 * | 12/2018 | Kim ......................... G02B 7/02 |
| 2018/0364456 A1 | 12/2018 | Kubota et al. |
| 2019/0004305 A1 * | 1/2019 | Duckett, III ......... G02B 23/243 |
| 2020/0142151 A1 * | 5/2020 | Kitagawa ............... G02B 7/023 |

FOREIGN PATENT DOCUMENTS

| | | | | |
|---|---|---|---|---|
| EP | 2357503 B1 | * | 10/2018 | ............ G02B 7/021 |
| KR | 20120026419 A | * | 3/2012 | |
| WO | WO-2018211678 A1 | * | 11/2018 | |

OTHER PUBLICATIONS

Daniel L. Marks et al., Multiscale Camera Objective with sub 2 Arcsec Resolution, 36 degree Field of View, 2014, pp. 1-3 [online], [retrieved on Nov. 8, 2022], retrieved from Internet <URL: https://opg.optica.org/view_article.cfm?gotourl=%2FDirectPDFAccess%2F2E0A65C2%2D9289%2D4A39%2D8AAFA5D6C57DE845%5>. (Year: 2014).*
Darryl Meister, High-Powered Lenses and Thicknesses, 2019, pp. 1-22 [online], [retrieved on Nov. 4, 2022], retrieved from the Internet <URL: http://opticampus.opti.vision/cecourse.php?url=high_powered/>. (Year: 2019).*
Lens Materials, 2010, pp. 1-7 [online], [retrieved May 25, 2023], retrieved from the Internet <URL: https://www.laramyk.com/resources/education/lens-options-and-materials/lens-materials/>. (Year: 2010).*
Michael R. Gaab, Instrumentation: Endoscopes and Equipment, 2013, pp. 1-11 [online], [retrieved Apr. 30, 2023], retrieved from the Internet <URL: http://dx.doi.org/10.1016/j.wneu.2012.02.032 >. (Year: 2013).*
Simon Thibault et al., Consumer Electronic Optics: How Small a Lens can be? The Case of Panomorph Lenses, 9192 Proceedings of SPIE 91920H-1 to 91920H-7 (2014). (Year: 2014).*
Melike Güzin Semercioğlu, Basis Parameters of Lens Design, 7 International Journal of Health Sciences Research Policy 209-220 (2022). (Year: 2022).*
S.J. Dobson et al., A New Rod-lens Relay System Offering Improved Image Quality, 22 Journal of Physics E: Scientific Instruments 450-455 (1989) (Year: 1989).*
Beau A Standish et al., In vivo Endoscopic Muti-beam optical Coherence Tomography, 55 Physics in Medicine & Biology 615-622 (2010). (Year: 2010).*
Dewen Cheng et al., Optical Design and Evaluation of a 4 mm Cost-effective Ultra-high-definition Arthroscope, 5 Biomedical Optics Express 2697-2714 (2014). (Year: 2014).*
Optic Spacers, Oct. 2019, pp. 1-4 [online], [retrieved Sep. 21, 2023], retrieved from the Internet <URL: https://www.thorlabs.com/newgrouppage9_pf.cfm?guide=10&category_id=220&objectgroup_id=4085>. (Year: 2019).*
Lens Barrel Assemblies, 2015, pp. 57-61 [online], [retrieved May 7, 2024], retrieved from the Internet <URL: https://web.archive.org/web/20151003031948/https://spie.org/samples/FG26.pdf>. (Year: 2015).*
Daniel Vukibratovich, Optical Instrument Structural Design, 2017, pp. 343-449 [online], [retrieved May 7, 2024], retrieved from the Internet <URL: https://www.taylorfrancis.com/chapters/edit/10.1201/9781315217635-37/optical-instrument-structural-design>. (Year : 2017).*
Dorsch; R., German Search Report for German Patetnt Application No. 10 2019 008 226.5, Jul. 15, 2020, pp. 1-4, Munich.
Pereda Cubián, D., European Search Report, Ap. EP20205479, Mar. 16, 2021, pp. 1-6, Munich.

* cited by examiner

LENS SYSTEM FOR A VIDEO ENDOSCOPE, ENDOSCOPE OBJECTIVE, VIDEO ENDOSCOPE, AND ASSEMBLY METHOD

CROSS REFERENCE TO RELATED APPLICATIONS

This application claims priority to German Patent Application No. 102019008226.5, filed Nov. 26, 2019, and entitled, "Video endoscope and handle for a video endoscope," and is incorporated herein by reference.

FIELD OF THE INVENTION

The present invention relates to a lens system for a video endoscope, to an endoscope objective comprising a corresponding lens system, to a video endoscope having such an objective, and to an assembly method for an endoscope objective.

BACKGROUND OF THE INVENTION

Endoscopes for medical or non-medical applications have an elongate shaft configured for being introduced into an internal cavity of a human or animal body or another object to be examined. The shaft may be rigid, semi-flexible, or flexible. Typically, the endoscope has a handle attached to a proximal (i.e. close to a user) end section of the shaft. In a distal (i.e. distant from a user) end section of the shaft an objective lens system is arranged for generating an image of an object field in the cavity of the body or object. In video endoscopes, which also are denoted electronic endoscopes, the generated endoscopic image is picked up by an electronic image sensor. The image sensor is usually arranged in the distal end section of the shaft having its sensor plane in an image plane of the objective lens system. The collected image data is then transmitted electronically through the shaft and ultimately to a display device and/or an image processing unit to display the endoscopic image to the user. Such video endoscopes are commonly denoted chip-on-the-tip (COTT) endoscopes. Reusable medical endoscopes require cleaning and sterilization after each use. In most cases reusable medical endoscopes are subjected to an autoclave process including high temperature and pressurized steam.

U.S. Application No. 2012/0007972 A1 discloses an objective lens for an endoscope that includes, in order from an object side, a front group having negative refractive power, an aperture stop, and a rear group having positive refractive power, wherein the front group includes a first lens which is a negative meniscus lens and a second lens which is a negative lens with a concave surface turned to the object side, and the rear group includes a positive third lens and a fourth lens made up of a positive lens and a negative lens cemented together. The optical surfaces of all lenses are spherical. The objective lens has an angle of view of 180° or more and has a comparatively long extension as measured from an object-side surface of the first lens to an image plane.

U.S. Application No. 2012/0016199 A1 relates to a capsule endoscope that includes an image pickup optical system for capturing an image of an object surface in the shape of a concave hemisphere. In order to widen an angle of view and to make the image surface coincide with the region of the image pickup surface over the entire angle of view, the image pickup optical system is configured to satisfy a condition expressed in terms of positions of a real image surface and a paraxial image forming position of a virtual object plane. A plastic lens is used for the image pickup optical system of the capsule endoscope. The capsule endoscope is to be used only once.

In U.S. Application No. 2014/0104707 A1, a small wide-angle objective optical system that is used in an endoscope is described. The objective optical system comprises, in order from an object side, an aperture stop, a positive first group, a second group, a positive third group, and a fourth group, wherein the third group is formed of a cemented lens consisting of a positive lens and a negative lens. The third group may include a diffractive optical element.

According to U.S. Application No. 2016/0235282 A1 a capsule endoscope is provided in which an objective lens unit includes, at the extreme object side, a lens which is a meniscus lens having negative power and disposed with a convex surface thereof towards the object side.

In U.S. Application No. 2011/0286112 A1 an objective optical system is disclosed that has a wide angle of view and can be used in endoscopes. The objective optical system includes, in order from an object side, a negative-powered first group, an aperture stop, a positive-powered second group, and a third group. Each group may be made up of a single lens. The lenses are manufactured from a resin material.

According to U.S. Pat. No. 9,257,470 B2 an imaging lens includes a first optical system and a micro-lens array provided between the first optical system and an imaging element. The first optical system includes an aperture stop, a first lens, a second lens, and a third lens. The second lens and the third lens are made of a plastic material. In US 2015/0077622 A1 an imaging lens for acquiring a range image and a visible image is disclosed that includes a first optical system and a micro-lens array provided between the first optical system and an imaging element. The first optical system includes an aperture stop, a first, a second, a third, and a fourth lens, wherein each of the second lens, the third lens, and the fourth lens includes a resin.

As disclosed in DE 10 2005 015 145 A1, an objective comprises, as seen from an object side, a first lens having positive power, a second lens having negative power, a third lens having positive power, and a fourth lens having negative power, being arranged along a common optical axis. The lenses are manufactured of a plastic material.

BRIEF DESCRIPTION OF THE INVENTION

Conventionally, endoscope objectives have a telecentric beam path in order to avoid vignetting. COTT endoscopes frequently employ objective lens systems having a long extension in an axial direction to achieve a near telecentric path. However, the available space in the distal end section of the shaft of an endoscope is very much limited. On the one hand, the outer diameter of the endoscope shaft is limited by an intended application of the endoscope, for example by the width of an opening or incision through which the shaft is to be inserted into a body cavity. On the other hand, several elements of the endoscope have considerable space requirements in the distal end section of the shaft, including, for example, illumination light guides and their related optics, and instrument channels, in addition to the endoscope objective.

Objective lens systems employed for cameras in mobile phones are not usually suitable for endoscopic applications. Perhaps most relevantly because mobile phone objectives have a comparatively large extension or footprint in a direction perpendicular to their optical axis. Further, mobile phone objectives do not fulfill the requirements imposed on re-usable endoscopes regarding cleaning and sterilization. Moreover, the optical image quality of mobile phones generally is inferior to that required in endoscopes.

It is also to be noted that high-resolution image sensors that are originally designed for mobile phones usually incorporate a micro-lens array that requires the objective lens system to have a relatively steep chief ray angle (CRA), the chief ray angle varying with increasing distance from an optical axis of the endoscope objective. Such micro-lens arrays may result in image deterioration, for example in color shifts in the edge areas of the image when used with standard COTT objectives. U.S. Pat. No. 10,598,918 B2, issued Mar. 24, 2020, to Duckett, which is hereby incorporated by reference, discloses video endoscope designs including an objective and image sensor in the distal region; the image sensor having a micro-lens array with micro-lens offsets designed for a designated chief ray angle.

It is an object of the present invention to provide an improved lens system for a video endoscope. In particular, it is an object of the invention to provide a lens system for a video endoscope that avoids or alleviates one or more of the above mentioned drawbacks relating, for example, to space requirements, sterilization, image quality and/or the use of high resolution electronic image sensors used in the mobile-phone industry. It is another object of the present invention to provide an improved endoscope objective for a video endoscope, a video endoscope having such an endoscope objective, and an improved assembly method for an endoscope objective.

The present invention, according to an aspect of the invention, relates to a lens system for a video endoscope. The video endoscope may be a rigid, semi-flexible, or flexible endoscope having a rigid, semi-flexible or flexible shaft, respectively. The shaft is configured for being inserted into an internal cavity of a human or animal body or another object to be viewed endoscopically. The video endoscope may be designed for medical or non-medical use. The lens system in particular is configured as an objective lens system for a video endoscope, wherein the objective lens system may be arranged in a distal end section of the shaft. Most preferably the video endoscope is a chip-on-the-tip endoscope having its electronic image sensor arranged in an image plane of the objective lens system.

In accordance with the present invention, the lens system comprises, in order from an object side, a cover glass, a first lens, a second lens, and one or more further lenses. The cover glass, the first lens, the second lens, and the one or more further lenses are arranged along an optical axis of the lens system. In the present application, the object side of an optical element, of the lens system or of an endoscope objective comprising the lens system is also denoted its "distal" side, as this side generally is that side that is distant from a user of the endoscope. Correspondingly, the image side of an optical element, the lens system or the endoscope objective is also denoted its "proximal" side. Nevertheless, the optical axis of the objective lens system may be inclined at an angle to a direction to the user, depending on the design of the endoscope.

The first lens, the second lens, and the one or more further lenses each are single lenses, that is, all lenses are separated by an air gap or touch an adjacent lens at most pointwise. Thus, the lens system is free from compound lenses and does not include a cemented pair, triplet or multiplet. Moreover, none of the lenses is cemented to or integral with any other optical element having refractive optical power, such as a diffractive optical element.

According to the present invention, an aperture stop is arranged on the object side of the second lens, i.e. distally from the second lens. In particular, the aperture stop may be arranged distally from the first lens, for example between the cover glass and the first lens, or the aperture stop may be arranged between the first lens and the second lens. The aperture stop may be arranged directly on an optical surface of the cover glass, or of the first or second lens, or may be arranged separate from the cover glass and the lenses. The optical surfaces are those surfaces of the lenses and the other optical elements of the lens system that are arranged along the optical axis and that are passed by the image light to be focused on the image sensor. In particular, the optical surfaces of the lenses may be refractive surfaces of the lenses, i.e. surfaces having refractive power.

Further in accordance with the present invention, at least all lenses situated on an image side of, i.e. proximal to, the aperture stop are aspherical lenses. Preferably both optical surfaces of each aspherical lens are aspherical. Most preferably, all lenses of the lens system are aspherical, and all optical surfaces of the lenses of the lens system are aspherical. The aspherical surfaces may be convex, concave, or may comprise convex, concave and/or plane portions. In particular the aspherical surfaces are rotationally symmetric with respect to an axis of symmetry of the respective lens, such that the convex, concave and/or plane portions form symmetric ring-shaped portions of the respective refractive surfaces of the lenses. The axes of symmetry of the lenses are aligned with each other and the optical axis of the lens system, such that the aspherical surfaces are rotationally symmetric with respect to the optical axis of the lens system. The lens system comprises, in addition to the lenses, a cover glass and may comprise further elements, such as one or more glass plates, filters, diaphragms, micro-lens arrays, etc. Those further elements are not comprised by the term "lens" in the present application.

Moreover, in accordance with the present invention, all lenses are made of glass, or in more general terms of an amorphous inorganic material, and/or of a crystalline material, such as sapphire, for example. In particular, none of the first lens, second lens and the one or more further lenses is made of a plastic or polymeric material or comprises a plastic or polymeric material. Further, at least one of the lenses has a refractive index n equal to or exceeding 1.66. The at least one lens having a refractive index $n \geq 1.66$ may be the first lens, the second lens, or one of the one or more further lenses. Preferably, the second lens has a refractive index $n \geq 1.66$, and/or a third lens has a refractive index $n \geq 1.66$, where the third lens is that one of the one or more further lenses immediately following the second lens along the optical axis in the proximal direction. Most preferably, the second and the third lens both have a refractive index $n \geq 1.66$. In the present disclosure, the refractive index n is the refractive index $n_d$ as defined conventionally, i.e. referring to a wavelength of 589 nm (corresponding to the sodium D line).

Due to the combination of the above-mentioned features, the lens system has a short overall length, permits providing a superior image quality, and can be adapted to commercial high-resolution image sensors. In particular the lens system can be adapted to high-resolution image sensors employed in mobile phones, which typically have a chief ray angle (CRA) exceeding 15° in edge portions of the sensor area and have a non-linear CRA function. The lens system can be designed, in particular, such that the ratio of an overall length to an image circle diameter is about 1.5 or less. Moreover, the lens system has improved thermal stability and may be able to withstand high temperatures, in particular temperatures of about 134° C. or more reached in an autoclave process, without significant deterioration of optical properties; therefore an endoscope comprising the lens system may be autoclavable, and thus the lens system can be employed in an objective of a re-usable endoscope. It has also been found that the use of glass or crystalline materials permits improved correction of chromatic aberration. All lenses being single lenses, limitations regarding the use and manufacturing of aspherical surfaces can be avoided. Due to the aspherical surfaces, distortion can be favorably corrected to be, for example, less than 10% up to an angle ω of 42.5° from the optical axis, and less than 50% up to an angle ω of 80° from the optical axis. The lens system may have a field of view (2ω) of about 160° or less. The lens system in accordance with the present invention is thus particularly well suited for use in an endoscope objective.

The lens system in accordance with the present invention can be designed such that an object distance is finite, that is, objects situated at a distance of a few or several centimeters can be imaged with high image quality on the image sensor. In particular, the object distance is less than about 50 cm, preferably less than about 30 cm, more preferably less than about 8 cm, or, for example, between about 1 and 10 cm.

According to preferred embodiments of the invention, the at least one lens having a refractive index n≥1.66 has a refractive index n≥1.7 or, most preferably, n≥1.8. Further, more than one lens, in particular the second and the third lens, may both have a refractive index n≥1.7 or n≥1.8. In this way, image quality can be further enhanced, permitting an improved correction of distortion and/or chromatic aberration.

According to a preferred embodiment of the invention, at least one lens of the lens system has an Abbe number ν of about or exceeding 70, more preferably about or exceeding 80. In particular, the at least one lens having an Abbe number ν≥70 or ν≥80 may be the first lens. In this way a further improved correction of chromatic aberration can be achieved. In the present disclosure, the Abbe number ν is the Abbe number $v_d$ as defined conventionally, i.e. relating to the Fraunhofer C, D, and F spectral lines (corresponding to wavelengths of 656.3 nm, 589.3 nm, and 486.1 nm, respectively).

Preferably, the lens system comprises at most three lenses. That is, the lens system comprises exactly three lenses, which are the first lens, the second lens, and the third lens. Thus, for example, the lens system may comprise a total of six refractive optical surfaces, all of which are aspherical. In this way a particularly simple design permitting high-quality image correction can be provided.

Preferably, the first lens has a positive refractive power. In particular, the first lens may be a bi-convex lens. Here and in the following the terms "refractive power", "convex" and "concave" relate to such surface portions of the respective lenses that are adjacent to the optical axis of the lens system or are crossed by the optical axis. The first lens may have, for example, an object-side surface comprising, in an inner section adjacent to the optical axis, a convex portion having a larger radius of curvature and an image-side surface comprising, in an inner section, a convex portion having a smaller radius of curvature. In this way, image quality and, in particular, adaptation to a CRA function of the image sensor can be improved.

The second lens may be, in an embodiment of the invention, a positive meniscus lens having its convex surface directed towards the image side. In an alternative embodiment the second lens may be a bi-concave lens having a smaller radius of curvature on its object-side surface and a larger radius of curvature on its image-side surface. The third lens preferably is a positive or negative meniscus lens having its convex surface on its object side.

In accordance with a particularly preferred embodiment, at least one of the lenses has an aspherical surface having a turning point in surface inclination to the optical axis, as seen with increasing radial distance from the optical axis. In this way improved adaptation to a CRA function of the electronic image sensor, which may be highly non-linear as a function of radial distance from the optical axis and even may have one or more turning points, can be achievable.

Preferably, the cover glass is formed by a plane glass plate, having two plane surfaces extending parallel to each other and, in particular, approximately perpendicular to the optical axis. Further preferably, the aperture stop is arranged on the plane surface on the proximal or image side of the cover glass. The aperture stop may be separated by an air gap from the object-side surface of the first lens. The aperture stop may be formed by a coating on the proximal side of the cover glass, or may be a separate element.

In accordance with an advantageous embodiment of the invention, a plane glass plate is arranged between a last lens of the one or more further lenses, in order from the object side, and the image plane of the lens system. In the image plane an electronic image sensor of a chip-on-the-tip endoscope can be placed. Instead or in addition to the plane glass plate, a micro-lens array may be arranged adjacent to a sensor plane of the image sensor and thus between the image plane and the plane glass plate. The plane glass plate is advantageous in improving mechanical stability and adapting the focal length of the lens system. The glass plate and/or the image sensor may be equipped with an optical filter.

Here and in the following the diameter of a lens is defined as the maximum of the diameters of the object-side and the image-side refractive surfaces of the respective lens, wherein the diameter is measured in a radial direction, perpendicular to the optical axis of the lens system.

According to particularly preferred embodiment of the invention, the second lens has a larger diameter than the first lens. Thus, the larger one of the diameters of the two optical surfaces of the second lens exceeds the larger one of the diameters of the two optical surfaces of the first lens. Further preferably, the third lens has a larger diameter than the second lens. In case that the lens system comprises more than three lenses, in a further preferred manner a fourth lens of the lens system following the third lens in a proximal direction has a larger diameter than the third lens, and, if there are more than four lenses, each consecutive lens has a larger diameter than the respective preceding lens, in order from the object side. Thus, the diameters of the lenses increase towards the image side of the lens system or of an endoscope objective comprising the lens system. According to this aspect of the invention it has been found that in this way unobstructed imaging on a large, high resolution image sensor can be achieved, while towards a distal end of the lens system or the endoscope objective an overall diameter of the lens system or the endoscope objective decreases. This is particularly advantageous in cases when an endoscope being equipped with the lens system comprises further elements in a distal end section of its shaft, for example a light source or other illumination optics, an available space in the distal end section being strictly limited. Moreover, due to a small opening through which light enters into the lens system, stray light can be reduced.

In particular, an overall shape of the lens system is approximately frustoconical or frustopyramidal. That is, the lens system is tapered towards an object side, and a radial outer surface or an envelope of the lens system has an approximate shape of a truncated cone or a truncated pyramid, wherein a central axis of the cone or the pyramid coincides at least approximately with the optical axis of the lens system. In particular the cover glass forms the truncated end of the cone or pyramid. The base end of the truncated cone or the truncated pyramid is on the image side of the lens system. Preferably a maximal diameter or a maximal side length of the truncated cone or the truncated pyramid, which is the diameter at the base of the cone or the side length of the base of the pyramid, respectively, is less or at least does not exceed a maximal or corresponding side length of the electronic image sensor, including its substrate or packaging. In this way optimal use can be made of the available space in a tip of an endoscope, i.e. in the distal end section of the shaft of the endoscope.

In accordance with a particularly preferred embodiment of the invention, at least the first lens and the second lens, and preferably the one or more further lenses, each have a functional rim having a plane surface located outside a respective optical surface, i.e. at a larger radial distance from the optical axis than the respective optical surface. Preferably an object side of the respective functional rim exhibits the plane surface, most preferably both sides have plane surfaces. In particular, the functional rim of the second lens has a larger outer diameter than that of the first lens. Most preferably, the outer diameter of the functional rim of the third lens exceeds the outer diameter of the functional rim of the second lens and, if applicable, the outer diameters of the functional rims of the fourth or further lenses further increase towards the image side of the lens system. The functional rim of each lens may be formed integral with the lens, the lens including its functional rim being made in one piece; alternatively, the lens may be cemented into a ring-shaped element forming the functional rim. The cover glass may also exhibit a functional rim encompassing its image-side and object-side plane surfaces, or an outer portion of each surface may be regarded forming the functional rim. The functional rims permit holding the lenses in a fixed relationship to each other. Moreover, assembly of an endoscope objective comprising the lens system can be facilitated.

The invention also relates to an endoscope objective. The endoscope objective is an objective for a video endoscope, in particular for a chip-on-the-tip video endoscope. The endoscope objective comprises a lens system that is configured as described above, the lenses and other optical elements being held in a fixed relationship to each other.

In a preferred manner at least the first and the second lens each comprise a functional rim as described above, wherein the diameter of the second lens is larger than the diameter of the first lens, and the functional rim of the second lens is mounted on the functional rim of the first lens or on a spacer mounted on the functional rim of the first lens. In a further preferred manner, the third lens also comprises a functional rim, wherein the diameter of the third lens is larger than the diameter of the second lens, and the functional rim of the third lens is mounted on the functional rim of the second lens or on a spacer mounted on the functional rim of the second lens. Additionally, a functional rim may also be designed as a spacer of the subsequent lens. Further lenses, if applicable, also may have functional rims, each functional rim being mounted on the functional rim of the preceding lens or on a spacer mounted on the respective preceding functional rim, as seen from the object side. The functional rims may be mounted to each other or to the spacers by an adhesive, in particular by cementing a plane object-side surface of each functional rim to a corresponding plane image-side surface of the preceding functional rim or of a spacer arranged between the respective functional rims. The cover glass may also have a functional rim and may be mounted in a corresponding manner to the first lens. A further spacer may be employed for adjusting an axial distance to the image sensor. Advantageously the spacers may be formed of glass or of a crystalline or metallic material. The spacers may be ring-shaped, being arranged approximately symmetrical to the optical axis. In this way a particularly stable and robust arrangement can be achieved, and assembly of the lens system is facilitated.

The endoscope objective may have an overall shape of a truncated cone or a truncated pyramid. In particular, the lens system may be enclosed in an approximately frustoconical or frustopyramidal casing, formed preferably of an opaque material such as, for example, a metallic material. The casing may be fixed to an object side of an electronic image sensor or a carrier or a package of an electronic image sensor, for example by an adhesive. Most preferably the base of the frustoconical or frustopyramidal casing has a cross dimension that does not exceed the corresponding dimension of the image sensor, including a substrate or packaging of the image sensor. The casing or a further spacer can be configured for adjusting the distance to the image sensor such that the sensor area is held in the image plane. In this way the endoscope objective as a whole can be easily and precisely mounted to the image sensor and inserted as a unit, including the image sensor, into the endoscope shaft, having its optical axis preferably aligned with a longitudinal axis of the shaft and the image sensor being perpendicular to the longitudinal axis.

The invention further relates to a video endoscope having an elongate shaft, an endoscope objective arranged in a distal end section of the shaft, and an electronic image sensor arranged in an image plane of the endoscope objective. The elongate shaft is configured for being inserted into a body cavity of a human or animal body or into a cavity of another object. The video endoscope may be designed for medical or for non-medical applications. The shaft may be rigid, semi-flexible, or flexible. The video endoscope may comprise a head piece arranged at a proximal end of the shaft, the head piece remaining outside the body. The endoscope objective is configured as described above, comprising a lens system as described above.

In particular, the electronic image sensor is a high-definition (HD) image sensor having, for example, full-HD resolution. On a distal side of the image sensor, a micro-lens array may be arranged having a non-linear CRA function, and the lens system of the endoscope objective is adapted to the CRA function of the image sensor and the micro-lens array. In this way off-the-shelf high-resolution image sensors designed for mobile phones can be made use of, providing high image quality. In particular, the video endoscope may comprise an image sensor having a non-linear CRA function to which the lens system of the endoscope objective is adapted, and the lens system may at the same time be configured for high-quality correction of chromatic aberration and/or distortion and/or other aberrations. Further, shading or vignetting can be avoided. Moreover, the available space in the distal end section of the shaft of the video endoscope can be made optimal use of, and the endoscope may be autoclavable. Preferably, the video endoscope is a re-usable, autoclavable medical video endoscope.

According to a further aspect of the invention, a method is provided for assembling an endoscope objective for a video endoscope, in particular for a chip-on-the-tip video endoscope. In accordance with the method, a first lens, a second lens and one or more further lenses are provided, wherein all lenses are single lenses, at least the second and the one or more further lenses are aspherical, all lenses are made of glass or of a crystalline material, and at least one lens has a refractive index n approximately equal to or exceeding 1.66. The lenses may be produced by well-known manufacturing methods, for example by molding or grinding and polishing and/or by embossing the aspherical surfaces on lens blanks. Each lens has a functional rim having preferably plane surfaces on both sides, and the diameters of the lenses, as well as the outer diameters of the functional rims increase from the first to the second lens, from the second to the third lens, and, if applicable, from the third to further lenses. Moreover, a plane cover glass is provided having parallel plane surfaces on both sides.

According to the method, the first, second and the one or more further lenses are arranged in order from an object side and are centered such that the symmetry axes of the lenses coincide with each other, forming an optical axis of the endoscope objective. An aperture stop is provided on an image-side of the second lens, for example by means of a coating or by placing a ring-shaped diaphragm on or near the image-side surface of the cover glass or the first lens. The functional rim of the second lens is mounted on the functional rim of the first lens by cementing the object-side surface of the functional rim of the second lens to the image-side surface of the functional rim of the first lens; alternatively, a spacer is cemented to the image-side surface of the functional rim of the first lens, and the second lens is cemented with the object-side surface of its functional rim to the spacer. The third lens is mounted in a corresponding manner to the second lens, i.e. a functional rim of the third lens is cemented to the functional rim of the second lens or to a spacer mounted thereon. If applicable, further lenses are mounted in a corresponding manner, following the third lens in a proximal direction. The cover glass that may include the aperture stop, is mounted in a corresponding manner to the first lens, in particular a functional rim or an outer portion of the cover glass is cemented to an object-side surface of the functional rim of the first lens. The last lens on an image side of the lens assembly may be cemented to a spacer that can be mounted to a glass plate that serves as a protective cover for an electronic image sensor, wherein the spacer provides for such an axial distance that the sensor plane is arranged in the focal plane of the lens system. The mentioned steps of providing the aperture stop and mounting the lenses, the spacers and the cover glass may be performed in an order different from the one described.

In a consecutive step, the assembly of lenses, cover glass and, if applicable, spacers, is shaped into a frustoconical or frustopyramidal shape. For example, the lens assembly may form a more or less rectangular or cylindrical block; in this case the outer surfaces of the block are machined, for example by grinding or cutting, to attain the frustoconical or frustopyramidal shape. Alternatively, the elements mentioned may all be configured to form a corresponding shape when mounted.

The frustoconical or frustopyramidal-shaped lens assembly is thereafter inserted into a casing of corresponding shape and dimensions preferably made of an opaque material, such as a metallic material, and fixed therein for example by an adhesive. Most preferably, the casing provides for enclosing the elements of the lens system in a hermetically sealed manner. The casing may be fixed to a carrier or packaging of an electronic image sensor, adjusting a distance to the sensor area, or an additional spacer may be employed for adjusting the distance such that the image sensor is in the focal plane of the objective. The casing that may form a mechanical unit with the image sensor may be inserted into the distal end section of the shaft of a video endoscope.

The features of the invention as mentioned above and as described below apply not only in the combinations mentioned but also in other combinations or alone, without leaving the scope of the present invention.

Further aspects of the present invention will be apparent from the figures and from the description of particular embodiments that follows.

DETAILED DESCRIPTION OF THE INVENTION

Figure 1:
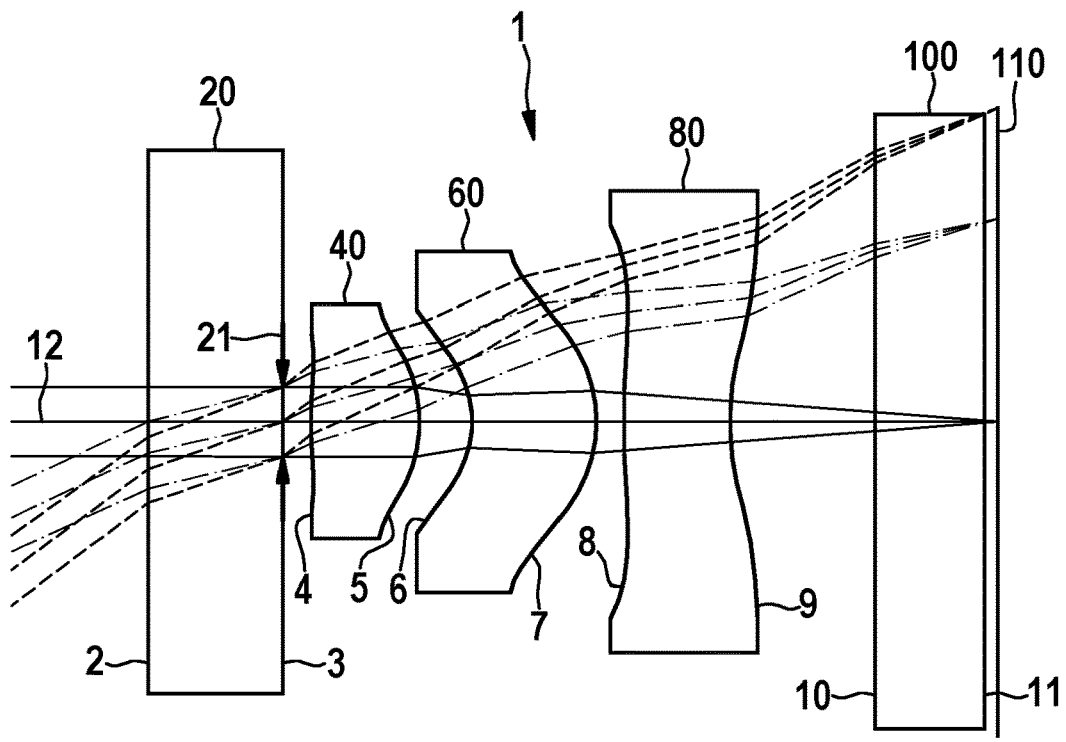
FIG. 1 shows a lens system according to a first embodiment of the present invention in an axial sectional view.
Figure 2:
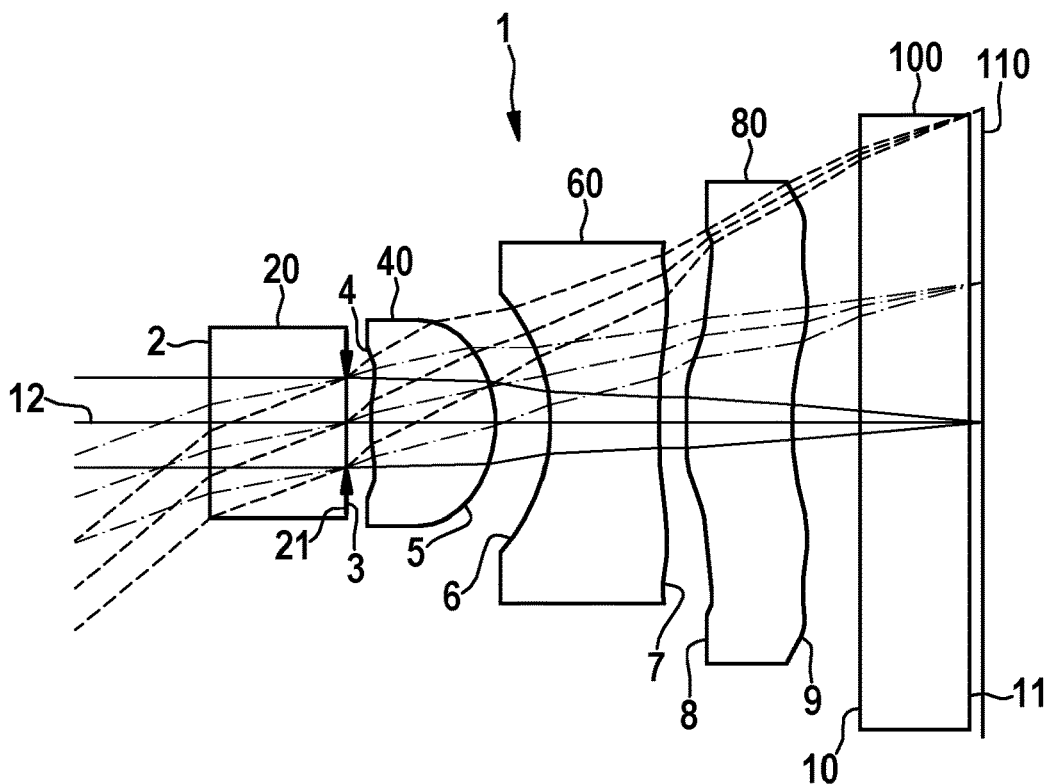
FIG. 2 shows a lens system according to a second embodiment of the invention in an axial sectional view.
Figure 3:
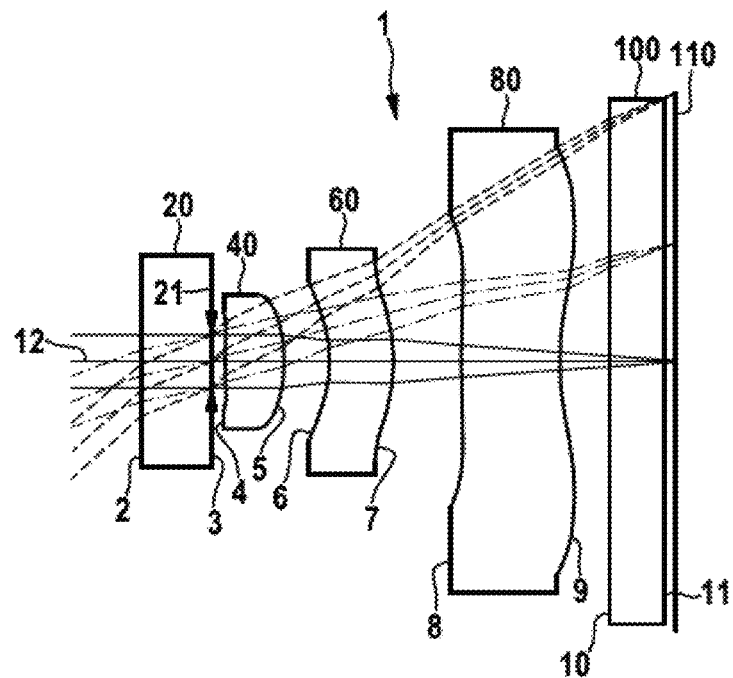
FIG. 3 shows a lens system according to a third embodiment of the invention in an axial sectional view.

In FIGS. 1, 2, and 3 exemplary embodiments of a lens system in accordance with the present invention are shown in an axial sectional view. According to each of the embodiments shown the lens system 1 comprises optical surfaces 2-11, which are, in order from an object side, plane surfaces 2, 3 of a cover glass 20, aspheric surfaces 4, 5 of a first lens 40, aspheric surfaces 6, 7 of a second lens 60, aspheric surfaces 8, 9 of a third lens 80, and plane surfaces 10, 11 of a glass plate 100. Further to the image side an electronic image sensor 110 is arranged having its sensor plane in the focal plane of the lens system 1. The image sensor 110 may be a CCD, CMOS or a MOSFET sensor, for example. Between the glass plate 100 and the image sensor 110 a micro-lens array is arranged (not shown). On the image-side surface 3 of the cover glass 20 an aperture stop 21 is formed, for example, by a ring-shaped diaphragm or by a coating on the surface 3 of the cover glass 20. FIGS. 1-3 also show exemplary rays entering into the lens system 1 from an object field, forming an image of the object field on the image sensor 110.

Each one of the lens systems 1 as depicted in FIGS. 1-3 comprises only three lenses, which are the first, second and third lens 40, 60, 80, each lens having two aspheric optical surfaces. The lenses 40, 60, 80, as well as the cover glass 20, the glass plate 100 and the image sensor 110 are arranged along the optical axis 12 of the lens system 1. The optical surfaces 4-9 of the lenses 40, 60, 80 are symmetric with respect to the optical axis 12. In the examples shown, the plane surfaces 2, 3 of the cover glass 10 and the plane surfaces 10, 11 of the glass plate 100 are perpendicular to the optical axis 12. As can be seen in FIGS. 1-3, the diameters of the lenses 40, 60, 80 increase with increasing lens number, i.e. from the object to the image side of the lens system 1. The diameter of each lens 40, 60, 80 is defined as the larger one of the diameters of its both optical surfaces, as measured from the optical axis 12. The diameter of the glass plate 100 exceeds that of the third lens 80. The cover glass 10 may have a diameter exceeding that of the first lens 40, however an outer portion of the cover glass 10 may be employed for mounting the lens system 1 or an endoscope objective (see below). The lenses 40, 60, 80 and the glass plate 100 are made of glass, while the cover glass 20 consists of sapphire.

Parameters describing the optical surfaces of the respective lens systems 1 according to the embodiments shown are given in Tables 1a-3b. In particular, Tables 1a, 2a, and 3a give the radius R of the inner portion of the respective refractive surfaces, the thickness d of the respective optical element or air gap, as measured on the optical axis 12 starting on the respective optical surface, the refractive index n, and the Abbe number ν of the respective optical element. The refractive index n and the Abbe number ν are defined in the conventional manner (see above). Tables 1b, 2b, and 3b give the coefficients of the aspherical surfaces 4-9, as defined in the conventional manner, indicating the displacement of a surface point in an axial direction as a function of various powers of r, where r is the distance from the optical axis 12.

According to the first embodiment and as can be seen in FIG. 1, the first lens 40 is, relating to respective inner portions of the optical surfaces 4, 5, a bi-convex lens having an almost plane object-side surface 4 and a convex image-side surface 5. The second lens 60 is a positive meniscus lens, having its convex surface on the image side. The third lens 80 is a negative meniscus lens, having its concave surface on the image side. Each of the lens surfaces 4-9 has a turning point in surface inclination to the optical axis, as seen in an axial section. That is, in a portion of the surface near the optical axis 12 the optical surface increasingly inclines in an object-side direction, but in an outer surface portion inclination in the object-side direction decreases with increasing distance radial distance r from the optical axis 12, or in an inner portion the surface inclination increases in the image-side direction with increasing radial distance r, and in an outer portion decreases with increasing distance radial distance r. The optical parameters of the embodiment of FIG. 1 are given in Tables 1a and 1b. The f-number of the first embodiment is 6.0, and the angle of view (2ω) is 73°.

TABLE 1a

Optical parameters of embodiment of FIG. 1

| Surface | R [mm] | d [mm] | n | ν |
|---|---|---|---|---|
| 2 | Infinity | 0.50 | 1.77 | 72 |
| 3 | Infinity | 0.10 | | |
| 4 | 2.5 | 0.40 | 1.50 | 81 |
| 5 | −0.57 | 0.22 | | |
| 6 | −3.7 | 0.46 | 1.69 | 53 |
| 7 | −0.47 | 0.05 | | |
| 8 | 2.6 | 0.40 | 1.90 | 21 |
| 9 | 0.97 | 0.53 | | |
| 10 | Infinity | 0.40 | 1.51 | 63 |
| 11 | Infinity | 0.05 | | |

TABLE 1b

Surface parameters of embodiment of FIG. 1

| Coefficient | Surface 4 | Surface 5 | Surface 6 | Surface 7 | Surface 8 | Surface 9 |
|---|---|---|---|---|---|---|
| Conic | −4.1E+01 | −2.8E+00 | −3.3E−01 | −8.8E−01 | −3.4E+00 | −1.3E+00 |
| Coefficient on $r^2$ | 0.0E+00 | 0.0E+00 | 0.0E+00 | 0.0E+00 | 0.0E+00 | 0.0E+00 |
| Coefficient on $r^4$ | −1.4E+00 | 5.1E+00 | 6.2E−01 | −4.6E−01 | −6.7E−01 | −9.5E−01 |
| Coefficient on $r^6$ | 1.2E+01 | −5.4E+01 | 7.6E+00 | 3.0E+00 | 8.7E−01 | 1.2E+00 |
| Coefficient on $r^8$ | −1.5E+02 | 1.8E+02 | 7.2E+01 | 4.2E−01 | −1.2E+00 | −1.7E+00 |
| Coefficient on $r^{10}$ | −5.4E+01 | −6.6E−09 | 9.4E+01 | 7.3E−03 | 1.8E−02 | 1.2E+00 |
| Coefficient on $r^{12}$ | 2.2E+01 | 0.0E+00 | −1.8E+02 | 0.0E+00 | 0.0E+00 | 0.0E+00 |

According to the second embodiment and as depicted in FIG. 2, the first lens 40 is, relating to respective inner portions of the optical surfaces 4, 5, a bi-convex lens having an almost plane object-side surface 4 and a convex image-side surface 5. The second lens 60 is a bi-concave lens. The third lens 80 is a positive meniscus lens, having its concave surface on the image side. Each of the lens surfaces 4, 6-9 has at least one turning point in surface inclination to the optical axis, as seen in an axial section. In particular, surface 7 has two turning points, and surfaces 8 and 9 each have three turning points. The optical parameters of the second embodiment are given in Tables 2a and 2b. The f-number of the second embodiment is 5.0, and the angle of view (2ω) is 81.5°.

TABLE 2a

Optical parameters of embodiment of FIG. 2

| Surface | R [mm] | d [mm] | n | ν |
|---|---|---|---|---|
| 2 | Infinity | 0.50 | 1.77 | 72 |
| 3 | Infinity | 0.10 | | |
| 4 | 2.6 | 0.46 | 1.43 | 95 |
| 5 | −0.42 | 0.20 | | |
| 6 | −0.80 | 0.40 | 1.69 | 53 |
| 7 | 0.00 | 0.10 | | |
| 8 | 1.4 | 0.40 | 1.69 | 53 |
| 9 | 2.9 | 0.25 | | |

TABLE 2a-continued

Optical parameters of embodiment of FIG. 2

| Surface | R [mm] | d [mm] | n | v |
|---|---|---|---|---|
| 10 | Infinity | 0.40 | 1.51 | 63 |
| 11 | Infinity | 0.05 | | |

TABLE 2b

Surface parameters of embodiment of FIG. 2

| Coefficient | Surface 4 | Surface 5 | Surface 6 | Surface 7 | Surface 8 | Surface 9 |
|---|---|---|---|---|---|---|
| Conic | 1.6E+01 | −3.2E−09 | −8.8E−01 | −5.6E+23 | 3.1E−01 | 5.2E+00 |
| Coefficient on $r^2$ | 0.00E+00 | 0.00E+00 | 0.00E+00 | 0.00E+00 | 0.00E+00 | 0.00E+00 |
| Coefficient on $r^4$ | −2.1E+00 | 4.6E+00 | 3.9E+00 | 1.5E+00 | 6.2E+00 | 4.9E+00 |
| Coefficient on $r^6$ | 7.7E+01 | −9.0E+01 | −1.1E+02 | −4.2E+00 | −6.9E+01 | −4.1E+01 |
| Coefficient on $r^8$ | −5.3E+03 | 1.1E+03 | 1.6E+03 | −2.7E+00 | 2.9E+02 | 1.3E+02 |
| Coefficient on $r^{10}$ | 1.3E+05 | −9.0E+03 | −1.3E+04 | 5.2E+00 | −6.2E+02 | −2.0E+02 |
| Coefficient on $r^{12}$ | −1.6E+06 | 3.6E+04 | 4.9E+04 | 1.5E+01 | 7.1E+02 | 1.4E+02 |
| Coefficient on $r^{14}$ | 1.0E+07 | −5.3E+04 | −7.1E+04 | 1.2E+01 | −4.1E+02 | −4.1E+01 |
| Coefficient on $r^{16}$ | −2.3E+07 | −4.7E+00 | −3.3E+02 | −3.7E+01 | 9.6E+01 | −2.2E−02 |

According to the third embodiment and as shown in FIG. 3, the first lens 40 is, relating to respective inner portions of the optical surfaces 4, 5, a bi-convex lens having an almost plane object-side surface 4 and a convex image-side surface 5. The second lens 60 is a positive meniscus lens, having its convex surface on the image side. The third lens 80 is a negative meniscus lens, having its concave surface on the image side. Each of the lens surfaces 4, 7-9 has at a turning point in surface inclination to the optical axis, as seen in an axial section. The optical parameters of the third embodiment are given in Tables 3a and 3b. The f-number of the third embodiment is 5.5, and the angle of view (2ω) is 79°.

TABLE 3a

Optical parameters of embodiment of FIG. 3

| Surface | R | d | n | v |
|---|---|---|---|---|
| 2 | Infinity | 0.50 | 1.77 | 72 |
| 3 | Infinity | 0.10 | | |
| 4 | 4.7 | 0.42 | 1.5 | 81 |
| 5 | −0.75 | 2.32 | | |
| 6 | −0.64 | 0.45 | 1.81 | 41 |
| 7 | −0.83 | 0.49 | | |
| 8 | 8.6 | 0.70 | 1.88 | 35 |
| 9 | 0.43 | 0.35 | | |
| 10 | Infinity | 0.40 | 1.51 | 63 |
| 11 | Infinity | 0.05 | | |

TABLE 3b

Surface parameters of embodiment of FIG. 3

| Coefficient | Surface 4 | Surface 5 | Surface 6 | Surface 7 | Surface 8 | Surface 9 |
|---|---|---|---|---|---|---|
| Conic | −7.1E−03 | −4.1E−06 | 2.8E−03 | −1.4E−02 | 2.0E−03 | −8.8E−01 |
| Coefficient on $r^2$ | −7.1E−03 | −4.1E−06 | 2.8E−03 | −1.4E−02 | 2.0E−03 | −8.8E−01 |
| Coefficient on $r^4$ | −1.3E+00 | 1.2E+00 | 1.6E+00 | 9.8E−01 | −6.9E−02 | −1.6E−02 |
| Coefficient on $r^6$ | 8.3E+00 | −7.6E+00 | −4.9E+00 | −7.9E−01 | −1.4E−01 | 2.3E−02 |
| Coefficient on $r^8$ | −1.0E+02 | 1.4E+01 | 5.2E+00 | 2.6E−01 | 1.0E−01 | −7.4E−03 |

In each of the embodiments shown in FIGS. 1-3 the lens system 1 is adapted to a full-HD image sensor, for example an OV5670 image sensor having a 1920×1080 pixel array. The image circle diameter is, for example, about 2.5 mm. The object distance is between about 10 and 100 mm, for example about 15 mm or 70 mm.

Figure 4:
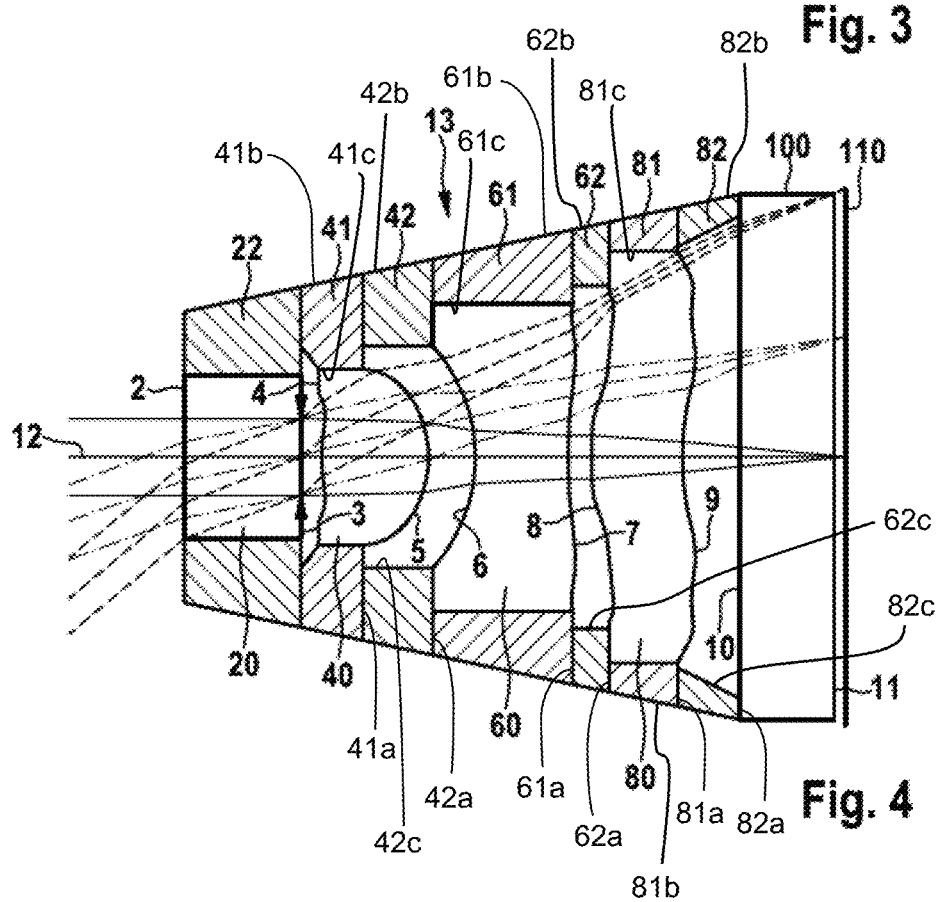
FIG. 4 shows a lens assembly according to an exemplary embodiment, in an axial sectional view.

As shown in FIG. 4, each of the lenses 40, 60, 80 has a functional rim 41, 61, 81, which may be integral with the respective lens or may be formed separate and cemented to the respective lens. Each of the functional rims has plane surfaces on the object side as well as on the image side. The plane surfaces 41a, 61a, 81a is formed on an image side of a respective rim 41, 61, 81 and includes a first peripheral portion 41b, 61b, 81b and a first inner portion 41c, 61c, 81c, the first peripheral portion 41b, 61b, 81b is concentric to a corresponding first inner portion 41c, 61c, 81c. The plane surfaces 41a, 61a, 81a, extend perpendicular to the optical axis 12. Further, ring-shaped spacers 42, 62 are arranged between the respective functional rims 41, 61, 81. Moreover a further spacer 82 is provided between the glass plate 100 and the functional rim 81 of the third lens 80. The spacers 42, 62, 82 have plane surfaces on both sides and are cemented with their plane surfaces to the respective adjacent plane surfaces of the functional rims 41, 61, 81, and the glass plate 100. In particular, the spacers 42, 62, 82 include a second planar surface 42a, 62a, 82a formed on a side opposite of the image side, the second planar surface 42a, 62a, 82a includes a second peripheral portion 42b, 62b, 82b and a second inner portion 42c, 62c, 82c. The second peripheral portion 42b, 62b, 82b is concentric to the second inner portion 42c, 62c, 82c. Moreover, a functional rim 22 of the cover glass 20 that may be an outer portion of the cover glass 20 is cemented to the object-side surface of the functional rim 41 of the first lens 10. The functional rims 41, 61, 81 and the spacers 42, 62 have a thickness to hold the cover glass 20 and the lenses 40, 60, 80 at respective distances as indicated in the Tables. The spacer 82 has a thickness to hold the glass plate 100 at a distance such that the image sensor 110 is in the focal plane of the lens system 1.

In FIG. 4 the lens system 1 itself is configured as the second embodiment. However, the other embodiments may comprise functional rims and may be mounted in a corresponding manner. The assembly 13 of lenses 40, 60, 80 and cover glass 20, including the respective functional rims 41, 61, 81 and spacers 42 and 62, and the glass plate 100, is part of or forms an endoscope objective 15. Due to the lenses having increasing diameters in the proximal direction, the lens assembly 13 shown in FIG. 4 has an overall frustoconical or frustopyramidal shape with the tip of the cone or the pyramid pointing in the distal direction. The lens assembly 13 may be enclosed in a casing 14, thereby forming an endoscope objective 15, which may be a hermetically sealed unit. This is shown in schematic, simplified manner in a perspective view in FIGS. 5 and 6.

Figure 5:
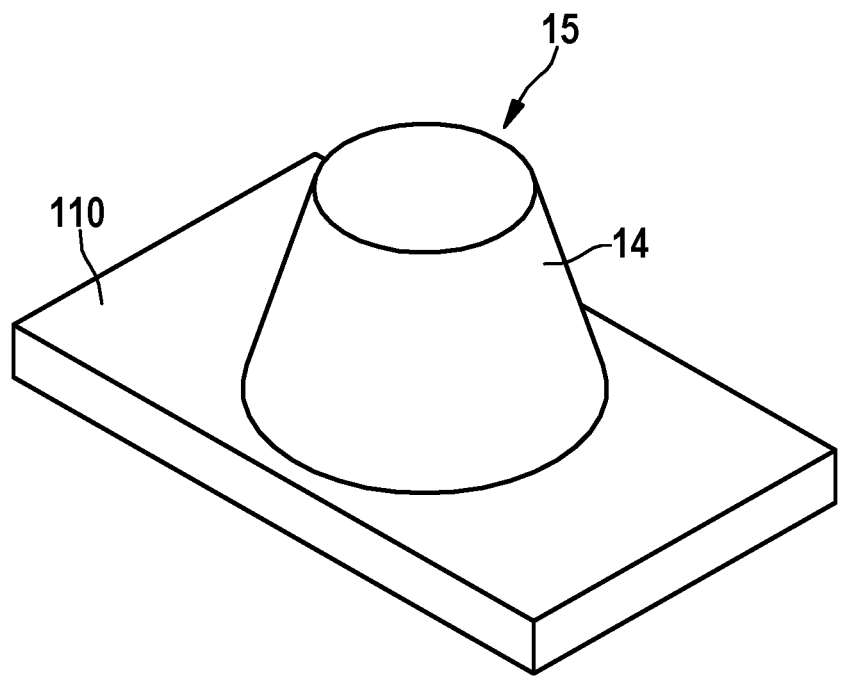
FIG. 5 shows in a simplified manner an endoscope objective and an electronic image sensor according to a first variation.
Figure 6:
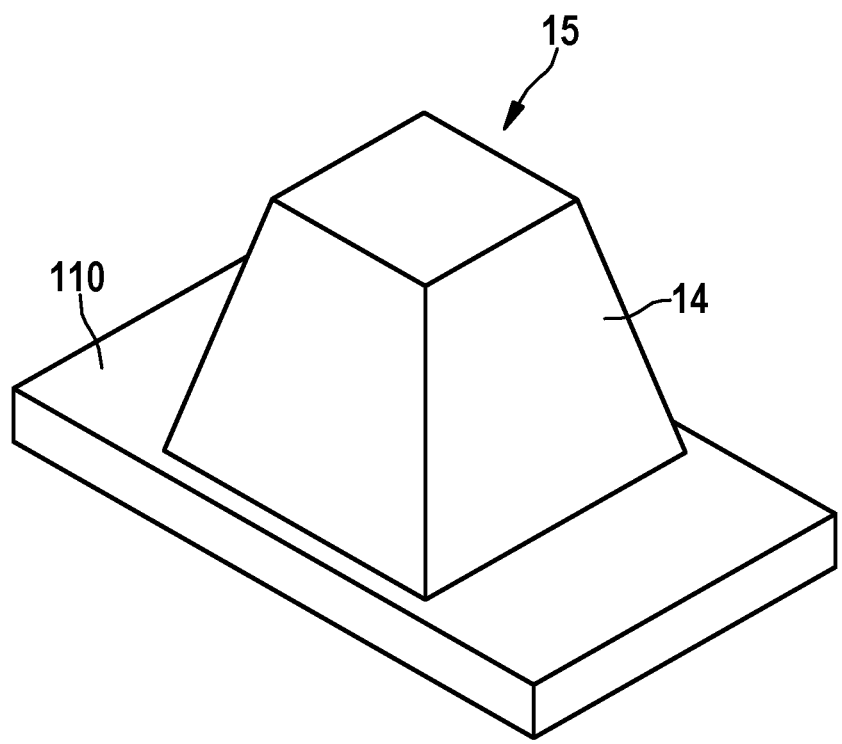
FIG. 6 shows in a simplified manner an endoscope objective and an electronic image sensor according to a second variation.

In a first variation and as depicted in FIG. 5, the casing 14 has frustoconical shape, the cover glass 20 being located in the truncated end of the cone. According to another variation shown in FIG. 6, the casing has frustopyramidal shape, the cover glass 20 being arranged in the truncated end of the pyramid. In this case the cover glass 20, as well as the lenses 40, 60, 80, and/or the glass plate 100 may be quadratic, rectangular, or circular, for example; in the latter case the functional rims 41, 61, 81 may have a quadratic outline in a radial sectional view. At the base end of the cone or pyramid the casing 14 is mounted on the image sensor 110, or on a carrier or packaging of the image sensor 110. In this way a compact imaging unit may be formed that can easily be inserted and mounted in the distal end section of an endoscope shaft. In an alternative embodiment the endoscope objective 15 may have overall cylindrical shape (not shown).

According to an exemplary assembly method for a video endoscope objective 15, a first lens 40, a second lens 60 and a third lens 80 are provided, all of which are single lenses, i.e. none of the lenses 40, 60, 80 is a compound lens or a cemented doublet, triplet, or multiplet (see FIGS. 1-3). The first, second, and third lenses 40, 60, 80 consist of glass or of a crystalline material, such as sapphire, for example. The second lens 60 and the third lens 80 each have a refractive index n exceeding 1.66, and the first lens 40 has an Abbe number ν exceeding 80, as indicated for the exemplary embodiments in Tables 1a, 2a, and 3a. Each of the lenses 40, 60, 80 is aspherical, having rotationally symmetric aspherical surfaces on both sides, as given in an exemplary manner in Tables 1b, 2b, and 3b. The lenses 40, 60, 80 may have been made by forming lens blanks for example by molding, cutting or grinding, with the aspherical surfaces being embossed on the lens blanks.

Moreover, as shown in FIG. 4, each one of the lenses 40, 60, 80 has a functional rim 41, 61, 81 having plane surfaces on both sides, the plane surfaces being formed outside the optical surfaces, i.e. at a larger radial distance from an axis of symmetry of the respective lens 40, 60, 80. The plane surfaces of the functional rims 41, 61, 81 are perpendicular to the axis of symmetry of each respective lens 40, 60, 80. The diameter of the second lens 60 exceeds the diameter of the first lens 40, i.e. in particular the second lens 60 has optical surfaces 6, 7 both of which have larger diameters than the optical surfaces 4, 5 of the first lens 40, and the outer diameter of the functional rim 61 of the second lens 60 is larger than the outer diameter of the functional rim 41 of the first lens 40. In a similar manner, the diameter of the third lens 80 exceeds the diameter of the second lens 60, referring to the optical surfaces as well as to the functional rims 61, 81.

Moreover, a cover glass 20 and a glass plate 100 are provided, each having opposing parallel plane optical surfaces 2, 3, 10, 11. An aperture stop 21 is arranged on an image-side surface 3 of the cover glass 20. The aperture stop 21 may be formed by providing a coating on the image-side plane surface 3 of the cover glass 20, or by mounting a diaphragm on the image side of the cover glass 20, for example. The cover glass 20 may also have a functional rim 22, which is formed by an outer peripheral portion of the cover glass 20.

The functional rim 41 of the first lens is mounted on the functional rim 22 of the cover glass 20 by cementing the object-side surface of the functional rim 41 to the image-side surface 3 of the cover glass 20 or the aperture stop 21 mounted on the cover glass 20. A first ring-shaped spacer 42 made of glass or metal is cemented to the image-side surface of the functional rim 41 of the first lens 40, the second lens 60 is centered with respect to the first lens 40 such that the respective axes of symmetry of both lenses 40, 60 coincide, and the functional rim 61 of the second lens 60 is cemented to the image-side surface of the first spacer 42. Moreover, a second ring-shaped spacer 62 is cemented to the image-side surface of the functional rim 61 of the second lens 60, the third lens 80 is centered with respect to the second lens 60 such that the respective axes of symmetry of both lenses 60, 80 coincide, and the functional rim 81 of the third lens 80 is cemented to the image-side surface of the second spacer 62. A third ring-shaped spacer 82 is cemented to the image-side surface of the functional rim 81 of the third lens 80, and the glass plate 100 is cemented to the image-side surface of the third spacer 82. The functional rims 41, 61, 81 and the spacers 42, 62, 82 each have an axial thickness that is adapted to form an air gap between the respective lenses 40, 60, and 80, as required for high-quality imaging.

The lens assembly 13 formed in this way has, depending on the outer circumferential shape of the functional rims 41, 61, 81, the spacers 42, 62, 82, and the glass plate 100, the shape of a truncated cone or a truncated pyramid, or is machined into an overall frustoconical or frustopyramidal shape. The lens assembly 13 is inserted into a casing 14 of corresponding shape, forming an endoscope objective 15.

An electronic image sensor 110 including a micro-lens array fixed to a sensor area of the image sensor can be arranged on an image side of the assembly 13 or the objective 15. The third spacer 82 and the glass plate 100 have thicknesses to define an axial distance to the image sensor 110 such that the sensor plane of the image sensor 110 is arranged in the focal plane of the lens assembly 13 when the image sensor or the micro-lens array is mounted directly adjacent to the image side of the glass plate 100, or when the casing 14 is fixed to a surface of the image sensor 110, or to a carrier or packaging of the image sensor 110 (see FIGS. 5 and 6). Alternatively, a gap between the lens assembly 13 or the casing 14 and the image sensor 110 may be adjusted such that the image sensor is in the focal plane of the lens assembly 13, and the image sensor 110 fixed in the corresponding distance to the casing 14 or fixed in the shaft of the endoscope.

For clarity not all reference numerals are displayed in all figures. If a reference numeral is not explicitly mentioned in the description of a figure, it has the same meaning as in the other figures.

REFERENCE NUMERALS

1 Lens system
2 Surface
3 Surface
4 Surface
5 Surface
6 Surface
7 Surface
8 Surface
9 Surface
10 Surface
11 Surface
12 Optical axis
13 Assembly
14 Casing
15 Endoscope objective
20 Cover glass
21 Aperture stop
22 Functional rim
40 First lens
41 Functional rim
42 Spacer
60 Second lens
61 Functional rim
62 Spacer
80 Third lens
81 Functional rim
82 Spacer
100 Glass plate
110 Image sensor

The invention claimed is:

1. A lens system for a video endoscope comprising, in order from an object side, a cover glass, a first lens, a second lens and one or more further lenses, wherein all lenses are single lenses and all lenses and the cover glass each comprise two optical surfaces, the optical surfaces being surfaces of the lens system that are arranged along an optical axis and that are passed by an image light, an aperture stop arranged directly on an optical surface of an image side of the cover glass, all lenses on an image side of the aperture stop are aspherical, all lenses are made of glass and/or of a crystalline material, and at least one lens has a refractive index n equal to or exceeding 1.66;
each of first lens, the second lens and the one or more further lenses includes a rim bounding a periphery of a corresponding one of the first lens, the second lens and the one or more further lenses; each rim includes a first planar surface having a first peripheral portion and a first inner portion, the first peripheral portion concentric to the first inner portion, formed on the image side of the respective rim; and
a plurality of spacers, wherein each spacer of the plurality of spacers is disposed between a corresponding pair of rims and includes a second planar surface formed on a side opposite of an image side of the respective spacer, the second planar surface having a second peripheral portion and a second inner portion, the second peripheral portion concentric to the second inner portion, the second planar surface abutting against the first peripheral portion of the first planar surface of a corresponding rim so as to space the second lens and the one or more further lenses apart from each other, the second lens and the one or more further lenses abutting against the second inner portion of a corresponding spacer and bound by a corresponding rim, wherein an overall shape of the lens system is frustoconical or frustopyramidal.

2. The lens system of claim 1, wherein the at least one lens having a refractive index of equal to or exceeding 1.66 has a refractive index equal to or exceeding 1.8.

3. The lens system of claim 1 wherein at least one lens has an Abbe number ν exceeding 70.

4. The lens system of claim 1, wherein the lens system comprises at most 3 lenses.

5. The lens system of claim 1, wherein the first lens has positive refractive power.

6. The lens system of claim 1, wherein at least one of the lenses has an aspherical surface having a turning point in surface inclination with respect to an optical axis.

7. The lens system of claim 1, wherein the aperture stop is formed by a coating on the image-side surface of the cover glass.

8. The lens system of claim 1, wherein the lens system comprises a plane glass plate arranged between a last lens, in order from the object side, of the one or more further lenses and an image plane of the lens system.

9. The lens system of claim 1, wherein the second lens has a larger diameter than the first lens.

10. The lens system of claim 1, wherein the rim has a plane surface at a larger radial distance from the optical axis than the respective lens's optical surfaces.

11. The lens system of claim 1, wherein each lens has a diameter, and each lens diameter is defined as a larger one of a diameter of the lens's object-side optical surface and a diameter of its image-side optical surface, as measured from the optical axis; and the diameters of the lenses increase from the object side to the image side.

12. The lens system of claim 1, wherein each lens is rotationally symmetric about an optical axis of all the lenses.

13. An endoscope objective for a video endoscope, wherein the endoscope objective comprises a lens system comprising, in order from an object side, a cover glass, a first lens, a second lens and one or more further lenses, wherein all lenses are single lenses, an aperture stop arranged on the object side of the first or the second lens, all lenses on an image side of the aperture stop are aspherical, all lenses are made of glass and/or of a crystalline material, and at least one lens has a refractive index n equal to or exceeding 1.66, wherein all lenses and the cover glass each comprise two optical surfaces, the optical surfaces being surfaces of the lens system that are arranged along an optical axis and that are passed by an image light, and wherein at least the first lens and the second lens each have a functional rim, each functional rim includes a first planar surface having a first peripheral portion and a first inner portion, the first peripheral portion concentric to the first inner portion, the first planar surface disposed on a plane orthogonal to an optical axis of the first lens and the second lens and having a plane surface at a larger radial distance from the optical axis than the respective lens's optical surface and a plurality of spacers, wherein each spacer of the plurality of spacers is disposed between a corresponding pair of functional rims and rests against the first peripheral portion of a corresponding functional rim so as to space the first lens, the second lens and the one or more further lenses apart from each other, the second lens and the one or more further lenses abutting against a corresponding spacer and a corresponding rim, and wherein an outer surface of the functional rims and the plurality of spacers define a frustoconical or frustopyramidal shape.

14. The endoscope objective of claim 13, wherein at least one of the lenses has an aspherical surface having a turning point in surface inclination with respect to an optical axis.

15. The lens system of claim 1, wherein each of the plurality of spacers is made of glass or metal and is cemented to the corresponding pair of rims.

16. The endoscope objective of claim 13, wherein each of the plurality of spacers is made of glass or metal and is cemented to the corresponding pair of functional rims.

* * * * *